United States Patent [19]

Schneider et al.

[11] 4,444,180

[45] Apr. 24, 1984

[54] SURGICAL INSTRUMENT FOR ENGAGING A BONY PART OF THE HUMAN BODY AND GUIDING A DRILL BIT INTO A SPECIFIC LOCATION IN THE BONY PART

[75] Inventors: Gerhard Schneider, Älta; Lars G. B. Peterson, Partille, both of Sweden

[73] Assignee: Aktiebolaget Stille-Werner, Stockholm, Sweden

[21] Appl. No.: 353,707

[22] Filed: Mar. 1, 1982

[51] Int. Cl.³ ............................................. A61F 5/04
[52] U.S. Cl. ............................................. 128/92 EB
[58] Field of Search ...................... 128/92 EB, 92 EA

[56] References Cited

U.S. PATENT DOCUMENTS

| 2,181,746 | 11/1939 | Siebrandt | 128/92 EA |
| 2,291,413 | 7/1942 | Siebrandt | 128/92 EA |
| 2,583,896 | 1/1952 | Siebrandt | 128/92 EA |
| 4,235,428 | 11/1980 | Davis | 128/92 EB |

FOREIGN PATENT DOCUMENTS 551446 1/1958 Canada .......................... 128/92 EA Primary Examiner—John D. Yasko

[57] ABSTRACT

A surgical instrument is provided for engaging a bony part of the human body and guiding a drill bit into a specific location in the bony part comprising, in combination, a pair of lever arms pivotably attached at a point intermediate their ends; locking means for locking the arms together in a fixed position with respect to each other; means on each arm on the same side of the pivot attachment for manipulating the arms in a swinging movement about the pivot; each arm on the other side of the pivot attachment being shaped so that the pair of arms can embrace the bony part during an operation; one of the arms carrying on one end on said other side a guide head having at least one through passage to guide a drill bit and the other arm carrying at one end on the said side an engagement head, the inner facing surfaces of the guide head and engagement head being shaped to fixedly engage said bony part, the through passage in the guide head being aligned along an axis which in the operating position of the instrument with the guide head and the engagement head engaging said bony part is directed towards and within the dimensions of the engagement head, so as to direct the drill bit to the selected specific location in the bony part.

9 Claims, 5 Drawing Figures

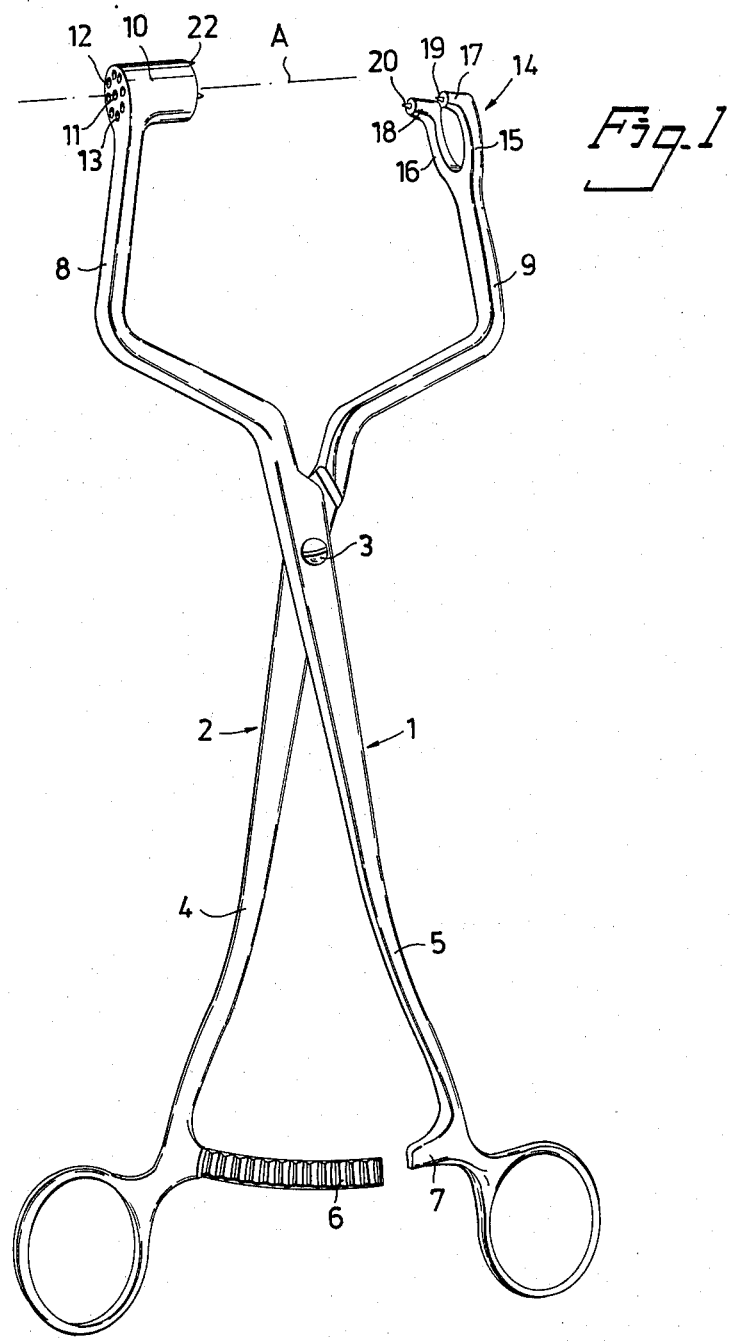

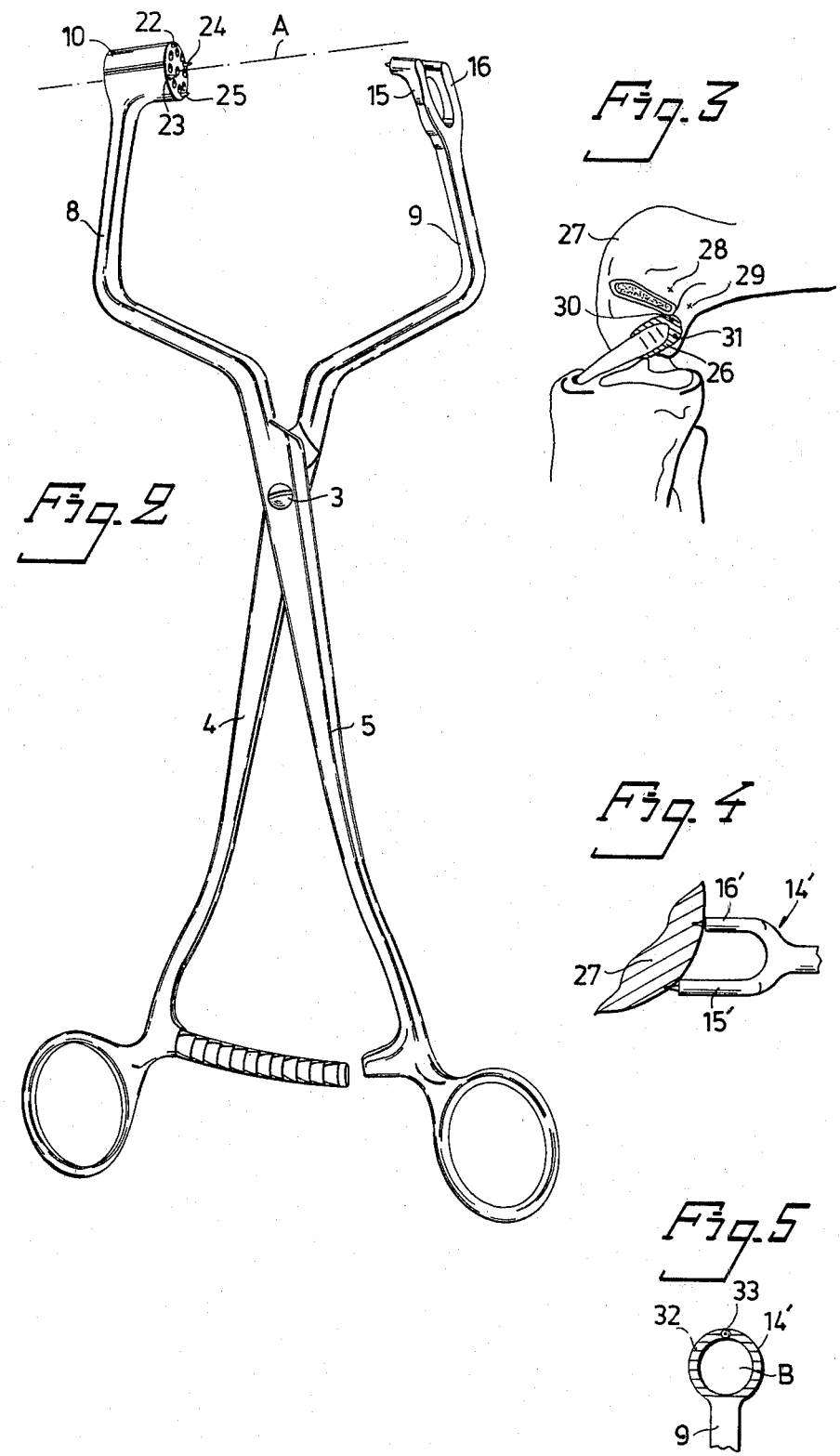

SURGICAL INSTRUMENT FOR ENGAGING A BONY PART OF THE HUMAN BODY AND GUIDING A DRILL BIT INTO A SPECIFIC LOCATION IN THE BONY PART

Surgical instruments for engaging bony parts of the human body and guiding a drill bit towards a specific location in the bony part have two pivotably attached lever arms, the end of one of which carries a guide means for the drill bit, shaped with jaws for clamping and holding together two sections of bone which are to be joined together. One or several holes are drilled through the bone sections, and then the bone sections are sewn together with sutures. The guide means for the drill bit can be slidably or pivotably mounted on the lever arm, and has one or several through passages for the drill bit. However, the available instruments do not permit alignment of the drill bit passage with sufficient accuracy for the more precise operations, for example, when a ruptured ligament is to be joined to a condyle.

The present invention provides a surgical instrument of this type, which permits drilling of a passage in a bony part with extreme precision, in any selected precisely aligned direction, and which, in contrast to prior art devices can be locked onto the bony part, for example, a condyle, in the most appropriate position for a precision ligament or tendon transplant operation.

The surgical instrument in accordance with the invention is arranged to engage a bony part of the human body and guide a drill bit into a specific location in the bony part, and comprises, in combination:

(1) a pair of lever arms pivotably attached at a point intermediate their ends;

(2) locking means for locking the arms together in a fixed position with respect to each other;

(3) means on each arm on the same side of the pivot attachment for manipulating the arms in a swinging movement about the pivot;

(4) each arm on the other side of the pivot attachment being shaped so that the pair of arms can embrace the bony part during an operation;

(5) one of the arms carrying on one end on said other side a guide head having at least one through passage to guide a drill bit; and (6) the other arm carrying at one end on the said other side an engagement head;

(7) the inner facing surfaces of the guide head and engagement head being shaped to fixedly engage said bony part;

(8) the through passage in the guide head being aligned along an axis which in the operating position of the instrument, with the guide head and the engagement head engaging said bony part is directed towards and within the dimensions of the engagement head, so as to direct the drill bit to the selected specific location in the bony part.

A preferred embodiment of surgical instrument in accordance with the invention is shown in the accompanying drawings, wherein:

FIG. 1 shows a perspective view of a surgical instrument of the forceps type according to the invention;

FIG. 2 shows a perspective view from the opposite side of the instrument shown in FIG. 1;

FIG. 3 illustrates in a simplified manner the attachment of a tendon using the device of FIGS. 1 and 2;

FIG. 4 is a detail view of an engagement head according to the invention in position engaging a bony part; and FIG. 5 shows another embodiment of engagement head.

The surgical instrument shown in FIGS. 1 and 2 has lever arms or forceps arms 1 and 2, desirably of stainless steel, joined together by means of a pivot 3. The manipulative shanks 4 and 5 on one side of the pivot pin 3 carry a conventional integral locking means composed of a toothed arcuate rod 6 joined to the shank 4 and extending towards the shank 5. The rod 6 interacts with a tooth (not shown) on a projection 7 on the shank 5 extending towards the shank 4. Locking takes place when the tooth on the projection 7 lies between two adjacent teeth on the rod 6, as the shanks 4 and 5 are pivoted towards each other by hand, manipulating the finger grips 4a, 5a. The two shanks 8 and 9 on the other side of the pivot 3 are shaped with an outwardly extending bend large enough to enable them to embrace a bony part such as part of a condyle. Fixedly attached to the end 8a of the shank 8 is a guide head 10 with at least one, and in this case nine, straight through parallel, cylindrical passages 11, 12, 13, sized to accomodate a drill bit. The longitudinal axis of the central passage 11 is marked in FIG. 1 by the line A. The opposite shank 9 has fixedly attached at its end section an engagement head 14 which in the illustrated embodiment is shaped as a fork with two prongs 15 and 16. Each prong has an inwardly curved end section, 17 and 18 respectively, extending towards the guide head 10. The end of each prong has a pin 19 and 20, respectively, shaped to penetrate into the bone tissue, and immovably hold the instrument against displacement of the guide head 14 after the instrument has been locked around the bony part, condyle or the like. The flat surface of the guide head 10 facing the engagement head 14 is also provided with four pins, 22, 23, 24, 25, also arranged to penetrate into the bone tissue, to prevent the guide head 10 from sliding or turning after the instrument has been locked to the condyle.

The pins 19, 20, 22, 23, 24, 25, can be replaced by other engaging means, such as knurls, blunt-tipped projections, or ribs, but pins are preferred.

In the position illustrated in FIGS. 1 and 2, the instrument is in the open position, and has not been clamped around the bony part into which the hole is to be drilled. However, in an operation on a ligament injury, the surgical instrument according to the invention is provided with shanks 8 and 9 of such a size that the axis A of the through passages 11, 12, 13 will, in the locked position of the instrument, lie between the pins 19 and 20, or within the open area defined by the dimensions of the engagement head. Thus, in contrast to what is possible with prior art instruments, it is very easy to visually determine the entry opening and exit opening of the drill bit passages, thereby ensuring that the drill bit passage or passages will be in correct alignment, for example, for the ligament or tendon transplant 26 which is to be attached to a condyle 27. If the alignment of the drill bit passages is not precise, the passages, for example, will direct the bit to points 28 and 29 instead of to the correct points 30 and 31, with the result that the ligament or tendon transplant will be misaligned, because the suture passing through the ligament or tendon transplant is wrongly directed by the drilled holes.

Inasmuch as the engagement head 14 which is applied to the point of attachment for the ligament or tendon transplant can be used to "sight" the axis A, it is possible when attaching the instrument to determine precisely the exact spot for drilling the hole in the bony part and obtain the correct points 30 and 31 shown in FIG. 3.

FIG. 4 is a detail view of an engagement head attached to shank 9 that has two prongs 15' and 16' in engagement with a curved surface of a bony part, one prong 15' being longer than the other prong 16', to ensure a better grip.

The engagement head may also be shaped as a ring, in which case the axis A will be located within the central opening through the ring, after the instrument has been clamped on. This ring may be circular, square, rectangular or triangular in shape.

FIG. 5 illustrates a circular ring 14' whose opening B is in alignment with axis A after the instrument has been clamped on the bony part. If there are a plurality of passages in the guide head 10, then the axes for all of these passages must pass through the opening B. The engagement surface of the engagement head 14' is in this case provided with knurls 32, which afford a good grip in combination with a tip 33.

The cylindrical guide head 10 need not be cylindrical, but can have any desired cross-sectional configuration.

Having regard to the foregoing disclosure, the following is claimed as the inventive and patentable embodiments thereof:

1. A surgical instrument for joining a ligament to a bony part of the human body, by immovably engaging a bony part of the human body and precisely guiding a drill bit into a specific precisely defined location in the bony part, comprising, in combination, a pair of lever arms pivotably attached at a point intermediate their ends; locking means for locking the arms together in a fixed position with respect to each other; means on each arm on the same side of the pivot attachment for manipulating the arms in a swinging movement about the pivot; each arm on the other side of the pivot attachment being shaped so that the pair of arms can embrace the bony part during an operation; one of the arms carrying immovably and fixedly mounted on one end on said other side a guide head having at least one through passage to guide a drill bit, and the other arm carrying immovably and fixedly mounted at one end on the said other side an engagement head having at least one opening therethrough defining an open area corresponding to the specific precisely defined location to be drilled into in the bony part; the inner facing surfaces of the guide head and engagement head being provided with a plurality of projections shaped to immovably and fixedly engage said bony part, the through passage in the guide head being aligned along an axis which in the operating position of the instrument, with the guide head and the engagement head engaging said bony part, is directed towards and within the dimensions of the open area defined by the opening through the engagement head, so as to precisely direct the drill bit along said axis to the selected specific precisely defined location in the bony part.

2. A surgical instrument according to claim 1 in which the guide head has a plurality of parallel through passages.

3. A surgical instrument according to claim 1 in which the guide head has a flat inner facing surface and the passage runs along an axis perpendicular to the surface of the bony part.

4. A surgical instrument according to claim 1 in which the engagement head is bifurcated and has two prongs which define therebetween the dimensions within which the drill bit is directed by the guide head.

5. A surgical instrument according to claim 4 in which one prong is longer than the other prong.

6. A surgical instrument according to claim 1 in which the engagement head is annular, having an opening which defines therewithin the dimensions within which the drill bit is directed by the guide head.

7. A surgical instrument according to claim 1 in which the engagement head carries on its inner facing surface a plurality of pins arranged to be pressed into the bony part.

8. A surgical instrument according to claim 1 in which the guide head carries on its inner facing surface a plurality of pins arranged to be pressed into the bony part.

9. A surgical instrument according to claim 1 in which both the guide head and the engagement head carry on their inner facing surfaces a plurality of pins arranged to be pressed into the bony part.

* * * * *